United States Patent [19]

Gelbein et al.

[11] 4,008,133
[45] Feb. 15, 1977

[54] PRODUCTION OF EPOXY COMPOUNDS FROM OLEFINIC COMPOUNDS

[75] Inventors: Abraham P. Gelbein, Plainfield; Joon Taek Kwon, Freehold Township, both of N.J.

[73] Assignee: The Lummus Company, Bloomfield, N.J.

[22] Filed: Mar. 23, 1976

[21] Appl. No.: 669,642

Related U.S. Application Data

[63] Continuation-in-part of Ser. No. 507,786, Sept. 20, 1974, abandoned.

[52] U.S. Cl. .............................. 204/80; 260/348 R
[51] Int. Cl.$^2$ ................. C25B 3/00; C07D 301/26; C07D 303/04; C07C 31/34
[58] Field of Search ........................ 204/79, 80, 81; 260/453 RX, 348 R, 348.6

[56] References Cited

UNITED STATES PATENTS

| | | | |
|---|---|---|---|
| 1,632,485 | 6/1927 | MacMullin | 260/453 R X |
| 2,694,722 | 11/1954 | Katz | 260/453 R X |
| 3,149,140 | 9/1964 | Nevin | 260/453 R X |
| 3,455,797 | 7/1969 | Courtier | 204/80 |
| 3,497,431 | 2/1970 | Kronig et al. | 204/80 |

OTHER PUBLICATIONS

Organic Hypohalites by Arthur et al., Chemical Reviews, vol. 54, No. 6, pp. 930, 931, Dec. 1954.
Heterocyclic Compounds with Three and Four-Membered Rings, Part I, pp. 96–98 by Weissberger, Pub. by Interscience (1964).

Primary Examiner—F.C. Edmundson
Attorney, Agent, or Firm—Marn & Jangarathis

[57] ABSTRACT

Olefin oxide is produced by reacting chlorine, obtained from an electrolysis cell, with a tertiary alkanol and an aqueous solution, containing sodium hydroxide and sodium chloride, obtained from the cathode of an electrolysis cell, to produce a tertiary alkyl hypochlorite. The hypochlorite is then reacted in a chlorohydrin reactor with an olefinically unsaturated compound and water, essentially free of chloride ions, to produce the corresponding chlorohydrin. The chlorohydrin is recovered and saponified with cell liquor, containing sodium hydroxide and sodium chloride, obtained from the cathode compartment of the cell to produce the olefin oxide.

18 Claims, 1 Drawing Figure

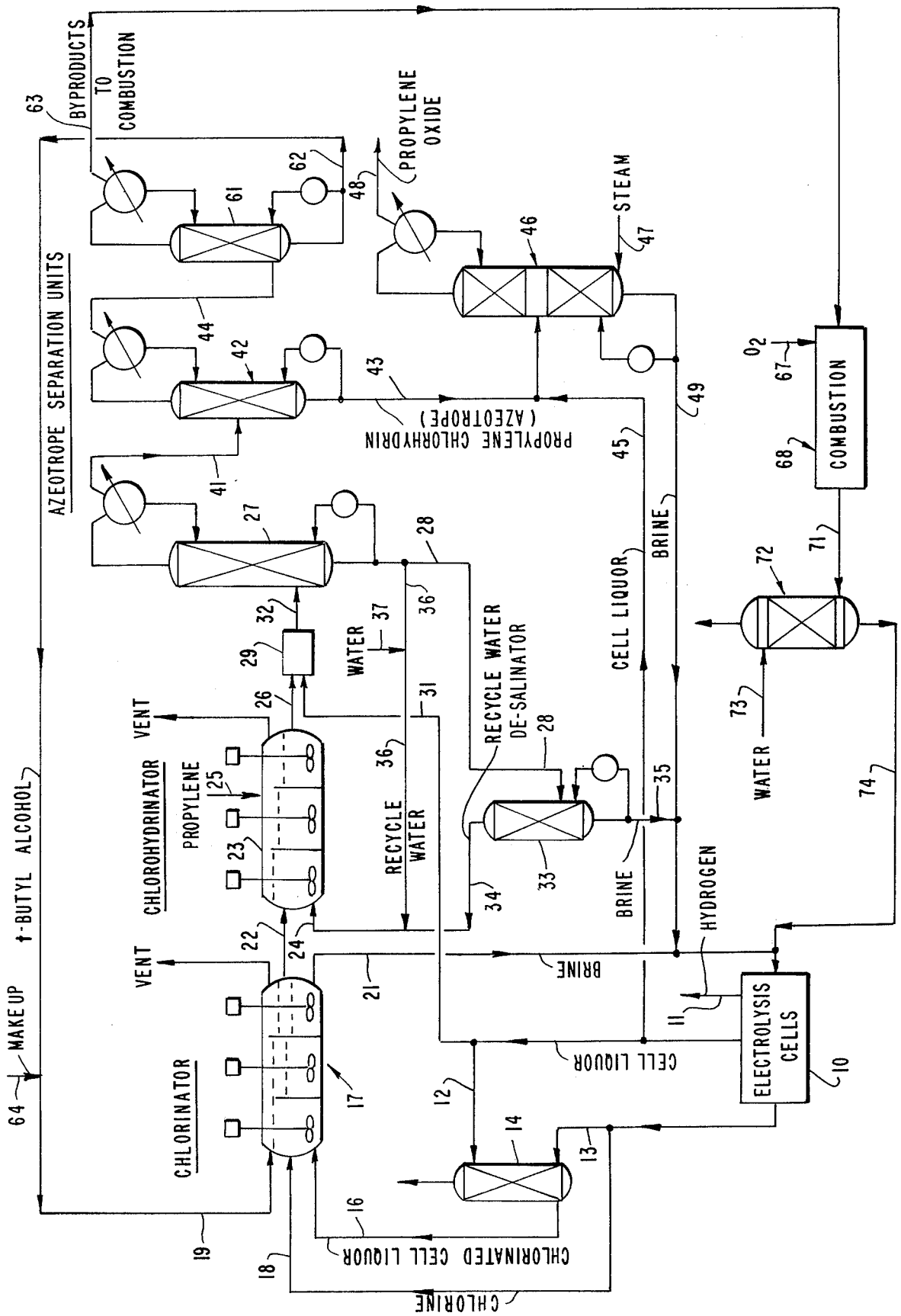

PRODUCTION OF EPOXY COMPOUNDS FROM OLEFINIC COMPOUNDS

This application is a continuation-in-part of U.S. application Ser. No. 507,786, filed on Sept. 20, 1974, now abandoned.

This invention relates to the production of epoxy compounds, and more particularly, to a new and improved process for producing epoxies from olefinically unsaturated compounds via the chlorohydrin route.

In the production of an epoxy compound, such as propylene oxide, via the chlorohydrin route, chlorine, water and propylene are reacted in a first reactor to produce hydrogen chloride and propylene chlorohydrin, with dichloropropane being produced as a by-product. The propylene chlorohydrin and hydrogen chloride are saponified and neutralized in a second reactor with calcium hydroxide to produce propylene oxide and calcium chloride. Currently, this process is considered to be uneconomical as a result of the consumption of chlorine and calcium hydroxide, and the difficulties associated with disposing of calcium chloride by-products.

Accordingly, an object of the present invention is to provide a new and improved process for producing epoxy compounds.

Another object of the present invention is to provide a new and improved process for producing epoxy compounds via a chlorohydrin.

Still another object of the present invention is to produce epoxy compounds from olefinically unsaturated compounds, without the consumption of chlorine and/or calcium hydroxide.

These and other objects of the present invention should be more readily apparent from reading the following detailed description thereof.

In accordance with the present invention, there is provided a process for producing epoxy compounds by initially producing a tertiary alkyl hypochlorite, which is then reacted with water and an olefinically unsaturated compound to produce the corresponding chlorohydrin, with the chlorohydrin being dehydrochlorinated to produce an epoxy compound. More particularly, gaseous chlorine is contacted in a first reaction zone with a liquid containing a tertiary alkanol and an alkali metal hydroxide to produce a tertiary alkyl hypochlorite. The tertiary alkyl hypochlorite is recovered, as an organic phase, and then contacted in a second reaction zone with an olefinically unsaturated compound and water, which is essentially free of chloride ions, to produce the corresponding chlorohydrin. Chlorohydrin produced in the second reaction zone is introduced into a third reaction zone, wherein the chlorohydrin is dehydrochlorinated to the corresponding epoxy compound. The dehydrochlorination can be effected by contacting the chlorohydrin with an aqueous solution of an alkali metal hydroxide; e.g., sodium hydroxide.

In accordance with a preferred procedure of the present invention, the hereinabove described process for producing an epoxy compound is integrated with an electrolytic process for producing chlorine, whereby the epoxy can be produced from olefin and water, as net starting materials, with the minimization of unwanted by-product production.

In accordance with the preferred aspect of the present invention, gaseous chlorine is produced in an electrolytic cell by the electrolysis of an aqueous brine solution, with chlorine being produced at the anode and hydrogen at the cathode. The gaseous chlorine produced in the electrolysis cell is reacted with a tertiary alkanol and an aqueous solution, containing sodium hydroxide and sodium chloride, obtained from the cathode compartment of the electrolytic cell to produce a tertiary alkyl hypochlorite. An organic phase, containing the tertiary alkyl hypochlorite is recovered from the first reaction zone and contacted in a second reaction zone with an olefinically unsaturated compound and water, which is essentially free of chloride ions, to produce the corresponding chlorohydrin. The chlorohydrin is recovered from the second reaction zone, either as an organic phase or in admixture with water and contacted with an aqueous solution of sodium hydroxide and sodium chloride, obtained from the cathode compartment of the electrolytic cell, to produce the corresponding epoxy compound, which is recovered as reaction product.

In accordance with the preferred procedure, the aqueous solution recovered from the first and third reaction zones containing sodium chloride is recycled to the electrolytic cell. The tertiary alkanol produced in the second reaction zone can be separated from the second stage reaction product or introduced into the third reaction zone along with the chlorohydrin, and subsequently recovered from the third reaction zone product for recycle to the first reaction zone.

The electrolysis cell used for producing chlorine from an aqueous brine may be any one of the wide variety of electrolytic cells known in the art, and is preferably of the diaphragm type. The cathode and anode may be any one of the wide variety of cathodes or anodes conventionally used in the art, with the anode generally being graphite and the cathode generally being iron. The details of the operation of the cell, except insofar as the electrolyte is concerned, form no part of the present invention and, accordingly, no further discussion in this respect is needed for an understanding of the present invention. The operation of such a cell is described, for example, in the U.S. Pat. No. 3,427,325.

In accordance with the present invention, the electrolyte fed to the anode has a sodium chloride concentration from about 170 to about 400 grams per liter of water, and preferably from about 280 to about 400 grams per liter of water. In the electrolytic cell, chlorine is produced at the anode and hydrogen is produced at the cathode, as represented by the following equation:

(1) $2 NaCl + 2 H_2O \rightarrow Cl_2 + 2 NaOH + H_2$

Chlorine produced in the electrolytic cell is introduced into a hypochlorite production reaction zone wherein the chlorine is reacted with a tertiary alkanol, preferably a tertiary alkanol having from 4 to 6 carbon atoms, and most preferably tertiary butanol or tertiary amylalcohol, and sodium hydroxide in an aqueous brine solution, obtained from the electrolytic cell, as represented by the following equations:

(2) $Cl_2 + 2 NaOH \rightarrow NaOCl + NaCl + H_2O$ (3) $NaOCl + ROH \rightarrow ROCl + NaOH$ (4) $Cl_2 + NaOH + ROH \rightarrow ROCl + NaCl + H_2O$ In general, the hypochlorite production reactor is operated at a temperature from about 5° to 220° F, preferably at a temperature from about 32° to 160° F, a pressure from about 5 psia to 100 psia, preferably from about 10 psia to 50 psia.

In accordance with the present invention, in order to minimize the amount of free chlorine present in the alkyl hypochlorite organic phase introduced as feed to the chlorohydrin reactor, the hypochlorite production reaction should be effected without a substantial molar excess of chlorine with respect to sodium hydroxide (Equation 2). Accordingly, in order to minimize the quantity of free chlorine present in the hypochlorite reaction product, the molar ratio of chlorine to sodium hydroxide generally does not exceed about 1.05 to 1, and is preferably at about stoichiometric proportions; i.e., 1:1.

In accordance with a preferred operation, the hypochlorite production reaction is effected in a manner such that the alkyl hypochlorite is formed as a separate organic phase to thereby eliminate the necessity of extracting the hypochlorite from the aqueous phase. In accordance with the present invention, in order to provide a separate organic phase, the hypochlorite production reaction is effected at a chlorine to sodium hydroxide mole ratio of at least 0.5:1. Thus, in accordance with the preferred operation, the hypochlorite production reaction is effected with chlorine to sodium hydroxide mole ratios of from about 0.5:1 to 1.05:1, and preferably from about 0.9:1 to 1:1.

In regard to the amount of tertiary alkanol employed with respect to the amount of sodium hydroxide, it has been found that the use of high molar excesses of sodium hydroxide with respect to the tertiary alkanol tends to increase the solubility of the tertiary alkanol in the aqueous phase. In view of the fact that the aqueous phase recovered from the hypochlorite production reactor is employed as electrolyte in the electrolytic cell, and the presence of tertiary alkanol tends to decrease the efficiency of the electrolytic cell, it is preferred to operate the hypochlorite production reactor without a substantial molar excess of sodium hydroxide with respect to the tertiary alkanol. In general, the mole ratio of tertiary alkanol to sodium hydroxide is from about 0.75:1 to about 1.1:1, and preferably from about 1:1 to 1.1:1.

It is to be understood that the cell liquor could be partially chlorinated in a separate vessel by contact with a portion of the overall chlorine requirements to produce sodium hypochlorite, with the remainder of the chlorine requirements, the t-alkanol and partially chlorinated cell liquor being introduced into the hypochlorite production reaction. In such a two-step process, in general, no more than about one-half of the total chlorine requirements are employed in the first stage to produce the sodium hypochlorite.

An aqueous brine phase and an organic phase, containing the hypochlorite, are separately recovered from the hypochlorite production reactor. The aqueous brine phase may then be introduced into the electrolytic cell, as electrolysis feed whereby the chlorine values are recovered therefrom. In effecting the production of hypochlorite, some hypochlorite and/or tertiary alkanol may be soluble in the water phase, and such components may be recovered by extraction with a suitable solvent, such as carbon tetrachloride. The extraction can be effected in the hypochlorite production vessel or in a separate vessel.

The organic phase, recovered from the hypochlorite production reactor, comprised of the tertiary alkyl hypochlorite alone or in combination with an added organic extraction agent, is then introduced into the chlorohydrin production reactor. In the chlorohydrin production reactor, the tertiary alkyl hypochlorite, preferably tertiary butyl hypochlorite, is contacted with an olefinically unsaturated compound and water, which is essentially free of chloride ion, to produce the chlorohydrin, as represented by the following equation, using propylene as a representative olefin:

(5) $ROCl + H_2O + C_3H_6 \rightarrow ROH + C_3H_6OCl$

The production of chlorohydrin is preferably effected, as hereinabove indicated, with water which is essentially free of chloride ion in that it has been found that the presence of chloride ion, in the aqueous phase, reduces the production of the desired chlorohydrin product. The water employed as feed to the chlorohydrinator should not contain a chloride ion concentration in excess of 1 mole/liter, and preferably the chloride ion concentration should not exceed 0.1 mole/liter. Of course, zero chloride ion concentration is most preferred; however, economic considerations may not permit zero chloride ion concentration. The term "essentially free of chloride ions" encompasses a chloride ion concentration of from 0 to 1 mole of chloride ions per liter of water. Furthermore, the presence of chlorine in the chlorohydrin production reactor should be avoided in that such chlorine is converted to the dichloro derivative, rather than the desired chlorohydrin; however, as a result of equilibrium considerations, some dissolved chlorine is introduced with the tertiary alkyl hypochlorite. The amount of free chlorine is maintained as low as possible, and generally does not exceed about 7 moles of chlorine per 100 moles of hypochlorite. It is to be understood that greater amounts of chlorine could be present, but such greater amounts reduce the yield of chlorohydrin.

The chlorohydrination of the olefin, with the tertiary alkyl hypochlorite, in water, is preferably effected at a temperature from about 32° to about 160° F, and preferably at a temperature from about 70° to about 140° F, and a pressure from 1 psig to about 100 psig, preferably atmospheric pressure. It is to be understood, however, that such conditions are only illustrative of preferred conditions, and the selection of particular conditions is deemed to be within the scope of those skilled in the art from the teachings herein. The chlorohydrination is preferably effected by cocurrent contact in a multistaged stirred reactor, but it is to be understood that a countercurrent operation could be employed.

In accordance with a preferred feature of the present invention, the water employed in the chlorohydrinator is maintained in a loop separate and distinct from water present in other reactors in order to insure that the presence of chloride ion is minimized. In particular, the product from the chlorohydrinator is generally subjected to distillation in order to recover water, which, along with make-up water is introduced into the chlorohydrinator. In view of the fact that some hydrogen chloride is generated in the chlorohydrin production reactor, it may be necessary to treat the water phase to prevent a chloride ion concentration in excess of the permissible amounts. Thus, for example, the hydrogen chloride could be neutralized with cell liquor, and all or a portion of the recovered water subjected to evaporation to reduce the chloride ion concentration and thereby maintain the circulating water loop (including make-up water) at chloride ion concentrations which are suitable for the purposes of the present invention.

In accordance with the preferred aspect of the present invention, the product from the chlorohydrinator is subjected to fractional distillation to separate water from organics, with the organics being recovered in admixture with water; in particular, as the azeotrope. Thus, for example, in the production of propylene oxide, the organic-water mixture is subjected to fractional distillation to separate propylene chlorohydrin therefrom, which is introduced as feed to the saponification reaction. The propylene chlorohydrin is recovered in admixture with water; in particular, as the azeotrope. The remaining stream, including tertiary alkanol, water, and organic by-products, is subjected to fractional distillation to recover tertiary alkanol for recycle to the hypochlorite production reactor. In general, the tertiary alkanol is in admixture with water.

As an alternative procedure, the tertiary alkanol can be introduced into the saponifier along with the propylene chlorohydrin, with the tertiary alkanol being subsequently recovered from the saponification product for recycle to the hypochlorite production reactor.

As a further alternative, the propylene chlorohydrin can be recovered by an extraction procedure, rather than by azeotropic distillation.

The chlorohydrin recovered from the chlorohydrinator is introduced into a saponifier, wherein the chlorohydrin is dehydrochlorinated to produce the corresponding epoxy compound. In particular, such dehydrochlorination is effected by direct contact between the chlorohydrin and a suitable base, such as, sodium hydroxide. The feed to the saponification generally contains from about 3 to about 54, preferably from about 10 to about 50 weight percent chlorohydrin. In accordance with the preferred embodiment of the present invention, the saponification is effected with cell liquor obtained from the cathode compartment of electrolytic cell, which contains sodium hydroxide and sodium chloride, which reacts with the chlorohydrin to produce the epoxy, as represented by the following equation, using propylene chlorohydrin as a representative example:

(6) $C_3H_7OCl + NaOH \rightarrow C_3H_6O + NaCl + H_2O$

In general, the saponification and neutralization is effected at a temperature from about 150° to about 250° F, preferably, from about 200° to about 230° F, at the autogenous pressure of the system. The cathode cell liquor which is fed to the saponification zone, using a diaphragm cell as a representative electrolytic cell, generally contains from about 40 to about 140 grams of sodium hydroxide per liter of water and from about 110 to about 200 grams of sodium chloride per liter of water. As a result of the saponification and neutralization, the chlorohydrin is dehydrochlorinated to the corresponding epoxy compound and the hydrogen chloride is neutralized to sodium chloride. It is to be understood that the above conditions are illustrative of preferred conditions and the selection of particular conditions is deemed to be within the scope of those skilled in the art from the teachings herein.

The epoxy compound is recovered as a reaction product from the saponification zone, and the aqueous phase, containing sodium chloride, is recovered from the saponification zone and introduced into the electrolytic cell. If tertiary alkanol is present in the feed to the saponification zone, the tertiary alkanol is separately recovered for recycle to the hypochlorite production zone.

In accordance with the present invention, it should be apparent from equations (1) to (6) that the overall process is represented by the following equation, using propylene as a representative feed:

(7) $C_3H_6 + H_2O \rightarrow C_3H_6O + H_2$

Accordingly, epoxy and hydrogen are produced from olefin and water, without the production of unwanted by-products.

The olefinically unsaturated compound employed as feed in the present process may be any one of a wide variety of olefinically unsaturated compounds, including both mono-olefinically and di-olefinically unsaturated compounds. The olefinically unsaturated compounds generally employed as feed are represented by the following structural formula:

$$R_1 - CH = CH - R_2$$

wherein $R_1$ and $R_2$ are each separately either hydrogen; alkyl; and halo naphthyl and phenyl substituted alkyl; halo and alkyl substituted phenyl; naphthyl and halo- and alkyl substituted naphthyl; alkenyl and halosubstituted alkenyl; and $R_1$ and $R_2$ can be linked together to provide a cycloalkene (generally 5 to 10 carbon atoms). The alkyl and alkenyl groups generally contain 1 to 6 carbon atoms and the halo group is preferably iodo-, bromo-, or chloro-, most preferably chloro-. As representative examples of the most suitable feedstocks, there may be mentioned: alkenes having from 2 to 6 carbon atoms, preferably 2 to 4 carbon atoms with ethylene and propylene being particularly preferred; styrene; cyclohexane; stilbene; butadiene; chloroprene; allyl chloride, allyl bromide; bromoprene; cyclohexene, and cyclopentene. The epoxy compounds generally produced in accordance with the invention are represented by the following structural formula:

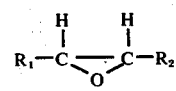

wherein $R_1$ and $R_2$ are as defined above.

The invention will be further described with respect to a preferred embodiment thereof, illustrated in the accompanying drawing wherein:

The drawing is a simplified schematic flow diagram of an embodiment of the process of the present invention.

The preferred embodiment will be particularly described with respect to the production of propylene oxide (1,2-epoxypropane), but it is to be understood that the embodiment is also applicable to the production of other epoxy compounds.

Referring to the drawing, there is shown an electrolytic cell 10, of a type known in the art, wherein, as known in the art, hydrogen is produced at the cathode, and chlorine at the anode, using sodium chloride as electrolyte. The hydrogen is withdrawn from the cell, as net product, through line 11.

Chlorine produced in cell 10 is withdrawn therefrom through line 12 and a first portion thereof in line 13 is introduced into a chlorinator 14 for chlorinating cell liquor wherein the chlorine countercurrently contacts cell liquor from the cathode compartment of cell 10, containing sodium hydroxide and sodium chloride, introduced into chlorinator 14 through line 15. In chlorinator 14, the chlorine chlorinates the cell liquor to convert a portion of the sodium hydroxide in the cell liquor to sodium hypochlorite, as defined in hereinabove Equation (2).

The partially chlorinated cell liquor, withdrawn from reactor 14 through line 16 is introduced into a hypochlorite production reactor 17, which is particularly shown is in the form of a multicompartmented stirred reactor. The remaining portion of the chlorine requirements for the hypochlorite production, obtained from cell 10, through line 18 is introduced into each of the compartments of reactor 17.

Tertiary alkanol, in particular, tertiary butyl alcohol, is introduced into reactor 17 through line 19. The chlorine, tertiary butyl alcohol and cell liquor are cocurrently contacted in reactor 17 at conditions hereinabove described to produce tertiary butyl hypochlorite.

An aqueous phase, containing sodium chloride, is withdrawn from reactor 17 through line 21 for introduction as electrolyte into cell 10.

An organic phase, containing tertiary butyl hypochlorite, withdrawn from reactor 17 through line 22 is introduced into a chlorohydrin production reactor 23, in the form of a multicompartmented stirred reactor, wherein the hypochlorite is cocurrently contacted with water, introduced into the first compartment through line 24, and propylene introduced into each compartment through line 25. The chlorohydrin production reactor is operated, as hereinabove described, to produce propylene chlorohydrin, and tertiary butyl alcohol, as co-reaction products. As hereinabove described, the water introduced into the chlorohydrin production reactor is maintained essentially free of chloride ion.

A chlorohydrin production effluent, containing propylene chlorohydrin, water, tertiary butyl alcohol, and by-products, such as dichloropropane, chloroacetone, bis-chloropropyl ether, etc., withdrawn from reactor 23 through line 26 is mixed in a suitable mixing vessel 29, with cell liquor in line 31, containing sodium hydroxide and obtained from the cathode compartment of the cell 10 to thereby neutralize any hydrogen chloride present in the solution and thereby minimize corrosion in column 27. The neutralized effluent in line 32 is introduced into a fractional distillation column 27, designed and operated to recover water as bottoms, and an organic-water azeotrope as overhead.

A first portion of the bottoms in line 28 is introduced into evaporator 33, to maintain the chloride ion concentration in the circulating water loop below the maximum permissible limit. The evaporator 33 is designed and operated to recover water, as overhead, in line 34, and an aqueous brine solution, as bottoms, in line 35, for introduction, as electrolyte into cell 10.

The remaining portion of the water bottoms from column 27, in line 36, is combined with make-up water in line 37, further combined with the water in line 34, and introduced into the chlorohydrinator 23 through line 24. It is to be understood that the relative amounts of water circulated through lines 28 and 36 are proportioned so as to insure that the water feed in line 24 has a chloride ion concentration which does not exceed 1.0 mole per liter, preferably not in excess of 0.1 mole per liter. It is also to be understood that all of the water bottoms could be subjected to evaporation in order to provide a water recycle having zero chloride ion concentration; however, the expense involved in such an operation, in most cases, does not justify such a further reduction in chloride ion concentration.

The organic-water azeotrope recovered, as overhead from column 27, in line 41, is introduced into a fractional distillation column 42 designed and operated to recover propylene chlorohydrin-water azeotrope, as bottoms, in line 43, and a remaining organic-water azeotrope, as overhead in line 44.

The propylene chlorohydrin-water azeotrope in line 43, is combined with cathode cell liquor, containing sodium hydroxide and sodium chloride, in line 45 and the combined stream introduced into a saponification (dehydrochlorination) reactor 46.

The saponification reactor 46 is comprised of a plurality of stages, and is operated at a temperature and pressure to effect saponification and neutralization of the chlorohydrin and stripping of propylene oxide product, with the heat requirements for such stripping preferably being provided by the introduction of steam into the bottom of column 46 through line 47. As hereinabove described, the cell liquor, containing sodium chloride and sodium hydroxide, contacts the propylene chlorohydrin and effects saponification and neutralization thereof to produce propylene oxide, with the sodium hydroxide neutralizing the hydrogen chloride released by the dehydrochlorination of the propylene chlorohydrin to produce sodium chloride.

Propylene oxide product is withdrawn from saponification reactor 46 through line 48 and an aqueous brine solution is withdrawn therefrom through line 49, combined with brine in lines 21 and 35, and introduced into cell 10 through line 51.

The overhead in line 44, comprised of water, tertiary butyl alcohol, and organic by-products, is introduced into a fractional distillation column 61, designed and operated to recover a tertiary butyl alcohol-water mixture, as bottoms, in line 62, and organic by-products, as overhead, in line 63. The tertiary butyl alcohol water mixture in line 62, is combined with make-up tertiary butyl alcohol in line 64 and introduced into reactor 17 through line 19.

The organic by-products, such as dichloropropane, chloroether, etc., in line 63 can be introduced into a combustion zone 68 with molecular oxygen, in line 69, to recover chlorine values therefrom by producing a combustion effluent containing the chlorine values primarily as hydrogen chloride. The combustion effluent, withdrawn through line 71 is introduced into a scrubbing zone, schematically indicated as 72, wherein the effluent is contacted with water, in line 73, to absorb the hydrogen chloride and recover the chlorine values as hydrochloric acid. An aqueous acid solution is withdrawn from zone 72 through line 74 and mixed with the brine in line 51. The hydrochloric acid functions to decompose any unreacted sodium hydrochlorite present in the recycle brine solution.

The hereinabove described embodiment is only illustrative of a preferred embodiment and, accordingly, within the scope and spirit of the invention the process may be practiced in a manner otherwise than as described with reference to the preferred embodiment.

Thus, for example, as hereinabove described, the propylene chlorohydrin may be recovered for introduction into the saponification reactor in a manner other than azeotropic distillation. Thus, for example, the propylene chlorohydrin could be recovered by a suitable extraction procedure. Similarly, the t-butyl alcohol could be introduced into the saponifier along with the chlorohydrin and subsequently recovered from the saponification effluent.

As a further modification the various reactions could be effected in a manner other than by cocurrent contact in stirred reactors, as described.

These and other modifications should be apparent to those skilled in the art from the teachings herein.

The invention will be further described with respect to the following examples, but it is to be understood that the scope of the invention is not to be limited thereby. Unless otherwise indicated, all parts and percentages are by weight.

EXAMPLE 1

Into a 2-l. capacity flask, 210.4 g. (2839 mmole) of t-butyl alcohol and 1.000.1 of an aqueous solution containing 113.6 g. (2839 mmole) of sodium hydroxide and 153.2 g. (2621 mmole) of sodium chloride were introduced at the ambient conditions. Gaseous chlorine was then charged into the mixture under agitation at a rate of about 100 mmole/min. until a total of 194.0 g. (2736 mmole) of chlorine was introduced, at which point the mixture showed a temperature of about 110° F.

When 78.0 g. (1100 mmole) of chlorine was introduced, the organic layer contained free chlorine only as its active chlorine. When 130.0 g. (1833 mmole) of chlorine was introduced, 33.2% of the alcohol was converted to the hypochlorite. At the termination of the reaction, 91.1% of the alcohol was converted to the hypochlorite, and the organic product layer contained 6.92 mole % of its active chlorine as the free chlorine.

EXAMPLE 2

The conversion of t-butyl hypochlorite to propylene chlorohydrin was carried out continuously in a reactor system consisting of three stirred reactors connected in series. Temperature was maintained at 120° F and pressure at one atmosphere, made up of primarily propylene. Water and t-butyl hypochlorite were fed to the system cocurrently to give a liquid residence time of 30 to 90 minutes. The feed t-butyl hypochlorite stream contained 6.29 mole % of its active chlorine content as free chlorine. The weight ratio of the t-butyl hypochlorite/water was from 0.032 to 0.054. In order to demonstrate an ability to generate high concentrations of the propylene chlorohydrin, the product (solution of propylene chlorohydrin and t-butanol in water) was successively recycled. In one recycle, the product stream contained 11.4 weight % t-butyl alcohol and 13.4 weight % propylene chlorohydrin, from a feed containing 9.0 weight % alcohol and 10.7 weight % chlorohydrin. After another recycle, the product stream contained 13.3 weight % alcohol and 16.4 weight % chlorohydrin, at 99.9% conversion of the active chlorine values. About 95.8 mole % or better selectively to the chlorohydrin was observed.

EXAMPLE 3

In a run similar to Example 1, 88.5 g. (1004 mmole) of t-amyl alcohol, 1068.1 g (6944 mmole) of carbon tetrachloride and 45.2 g. (1062 mmole) of sodium hydroxide in 972 g. of cell liquor were mixed together and chlorinated to give a carbon tetrachloride layer containing t-amyl hypochlorite.

In a 250-cc capacity pressure bomb, 114.2 g. (88.1 mmole active chlorine) of the organic product and 75 g. of water were introduced. The bomb was then sealed and charged with 45 psig propylene at 120° F and shaken for one hour. About 98.0 mole % of the active chlorine values were consumed to yield propylene chlorohydrin at an overall 93.5 mole % selectivity to the chlorohydrin (89.7 mmole).

EXAMPLE 4

The feasibility of dehydrochlorinating a concentrated solution of propylene chlorohydrin with a cell liquor is demonstrated in this example. The saponifier was made up of two vertically arranged packed columns, one inch internal diameter and three feet long, connected in series. An aqueous feed containing 39.29 weight % of propylene chlorohydrin (4370 mmole/l.) was pummped in at an average rate of 0.82 cc/min. at the center of the unit. A simulated cell liquor, containing 10.80 weight % of sodium hydroxide (3334 mmole/l.), was introduced at an average rate of 2.16 cc/min. at the same feed point. Steam was introduced to the bottom of the unit at 1.37 g/min. The overhead was collected at an average rate of 0.78 cc/min., while the reboiler was maintained at 110° C. After 51 minutes of continuous operation, propylene chlorohydrin conversion was 80.1 mole % at a selectivity to propylene oxide of essentially 100 mole %. The propylene oxide and unconverted propylene chlorohydrin was collected as an overhead product.

EXAMPLE 5

To a 1 liter capacity flask, equipped with a stirrer, 500 cc of water was charged at 50° C. While maintaining fast agitation, 0.80 cc/min. of t-butyl hypochlorite and allyl chloride were charged into the flask in separate streams. The reaction was conducted for one hour with temperature maintained at 50°–55° C. After completion of addition of the reactants, the mixture was agitated for 30 more minutes under a gentle flow of nitrogen.

The final reaction mixture consisted of an organic layer and aqueous layer. Allyl chloride charged during the reaction was 47.8 cc (44.8 g., 586 mmoles). The hypochlorite liquor charged (48.3 cc, 45.3g.) contained 410 mmoles of t-butyl hypochlorite and 8.7 mmoles of free chlorine, for a total active chlorine charge of 427 meq. The organic layer weighed 80.6 g. and the aqueous layer 501.1 g.

The aqueous layer contained a trace of hydrochloric acid and a small amount of t-butyl alcohol. In the organic layer traces of t-butyl hypochlorite, bis (monochlorohydrin) ether, t-butyl monochlorohydrin ether and trichloropropane were found. The organic layer was mostly made of t-butyl alcohol and the two dichloropropanols.

A 50.0 g. portion of the organic layer was charged into a 250 cc-volume flask, along with an 80.0 cc portion of a synthetic cell liquor (10.0 wt.% NaOH, 12.0 wt.% NaCl). The mixture was agitated with a magnetic stirrer, slowly brought to 80° C and held there for 10 minutes. The reaction temperature was then brought to the boiling temperature and the mixture distilled. The distillate was analyzed by GLC and was found to contain epichlorohydrin in an amount corresponding roughly to the epichlorohydrin-water azeotrope (75 wt.% epichlorohydrin, 25 wt% water, B.P. 88.5° C at 1 atm.).

EXAMPLE 6

The reaction given in the above example was repeated with styrene in the presence of 0.1 g. of hydroquinone stabilizer. The styrene charged was 49.3 cc (44.8 g., 430 mmole). The t-butyl hypochlorite charged was 48.0 cc (45.0 g., 408 meq. active chlorine), and the total reaction time was three hours. A trace of hydrochloric acid was found in the aqueous product layer. The product pattern in the organic layer was similar to that observed in the allyl chloride reaction. Saponification, as in Example 5, of the organic layer produced styrene oxide.

EXAMPLE 7

Into a 1000 cc-volume flask, 500 cc of water was charged and heated to 50° ± 5° C. Under fast agitation cyclohexene and t-butyl hypochlorite were charged in separate streams at a rate of 0.32 cc/min. for one hour. The reaction was continued for one more hour while maintaining the temperature at 50°–55° C. The total charges were:

| | |
|---|---|
| cyclohexene: | 19.8 cc (16.0 g., 195 mmoles) |
| t-butyl hypochlorite: | 19.4 cc (18.2 g. total, 154 mmoles) |
| chlorine: | 0.26 g. (3.6 mmoles) |

The final reaction mixture was then combined with 50 cc of a caustic/brine solution (10 wt% NaOH, 12 wt% NaCl, 78 wt% H$_2$O) at 60°–80° C with rapid agitation. The saponification reaction was allowed to proceed for 10 minutes, after which the mixture was cooled to approximately 25° C and extracted with benzene. The benzene extracts contained cyclohexene oxide, as determined by GLC.

EXAMPLE 8

The experiment in Example 7 was repeated with butadiene. The butadiene flow rate was maintained at 40 cc/min. NTP. The charge rate of t-butyl hypochlorite was kept at 0.16 cc/min. Hydroquinone (0.10 g.) was added as a polymerization inhibitor. The reaction was continued for two hours under fast agitation at 50°–55° C. While maintaining the temperature, the mixture was agitated for 30 more minutes under a gentle flow of nitrogen.

After cooling, the reaction mixture was treated with the cell liquor, as before. The reaction mixture was then distilled under vacuum (liquor temperature 35° C) to yield a distillate product containing 3,4-epoxy-1-butene, identified by GLC.

EXAMPLE 9

The test run in Example 8 was repeated with stilbene. 27.04 g. (150 mmoles) of trans-stilbene was partially dissolved in 500 cc of 20% aq. t-butyl alcohol at 50° C in a 1.0 l. flask. Under fast agitation, t-butyl hypochlorite was charged in at a flow rate of 0.16 cc/min. for 2 hours, while maintaining the reaction temperature at 50°–55° C. The mixture was agitated for one more hour under a gentle flow of nitrogen and cooled to the ambient temperature.

The resulting mixture was extracted with three portions of benzene. The benzene extracts were combined and treated with cell liquor, as before. The resulting organic layer was separated and was found to contain stilbene oxide, as determined by GLC.

The process of the present invention is particularly advantageous in that an epoxy compound can be produced without the production of unwanted by-products. Thus, for example, by proceeding in accordance with the teachings of the present invention, selectivity to propylene oxide is increased by reducing the production of by-products, such as, dichloropropane. In accordance with the present invention, propylene oxide selectivity in the order of at least 80% and generally in the order of 84% to 95% are readily achieved.

A further advantage of the present invention is that the liquid volume used in the dehydrochlorination is significantly reduced in that higher feed concentrations of chlorohydrin can be introduced into the saponification reactor as a result of the use of an organic medium. Thus, for example, chlorohydrin feed concentrations in the order of 30 wt% are readily achieved in the present invention, as compared to chlorohydrin concentrations in the order of 10 wt% used in prior art processes.

As still another advantage, the operation of the electrolytic cell is improved as a result of the electrolyte being free of inorganic impurities.

Numerous modifications and variations of the present invention as possible in light of the above teachings, therefore, within the scope of the appended claims, the invention may be practiced otherwise than as particularly described.

What is claimed is:
1. A process for converting an olefinically unsaturated compound to the corresponding epoxy compound, comprising:
   a. producing gaseous chlorine by the electrolysis of an aqueous brine solution in an electrolytic cell including an anode compartment and a cathode compartment, said gaseous chlorine being produced in the anode compartment and hydrogen in the cathode compartment;
   b. contacting in a first reaction zone gaseous chlorine from the cell, an aqueous solution containing sodium chloride and sodium hydroxide from the cathode compartment of the electrolytic cell and a tertiary alkanol to produce a tertiary alkyl hypochlorite;
   c. recovering from the first reaction zone an aqueous brine phase and an organic phase containing the tertiary alkyl hypochlorite;
   d. introducing the recovered aqueous brine phase as electrolyte into the electrolytic cell;
   e. contacting in a second reaction zone the organic phase containing the tertiary alkyl hypochlorite, an olefinically unsaturated compound and water, essentially free of chloride ions, to produce the corresponding chlorohydrin and a tertiary alkanol;
   f. recovering the chlorohydrin and tertiary alkanol from the second reaction zone;
   g. passing recovered tertiary alkanol to the first reaction zone;
   h. contacting in a third reaction zone the chlorohydrin with an aqueous solution of sodium hydroxide and sodium chloride obtained from the cathode compartment of the electrolytic cell to produce the corresponding epoxy compound;
   i. recovering epoxy compound and an aqueous brine solution from the third reaction zone; and j. introducing aqueous brine solution recovered from the third reaction zone into the electrolytic cell as electrolyte.

2. The process of claim 1 wherein the tertiary alkyl hypochlorite introduced into the second reaction zone contains no greater than 7 moles of active chlorine per 100 moles of tertiary alkyl hypochlorite.

3. The process of claim 2 wherein the aqueous solution containing sodium chloride and sodium hydroxide from the cathode compartment of the electrolytic cell is contacted with gaseous chlorine from the electrolytic cell prior to introduction into the first reaction zone to produce sodium hypochlorite, whereby the aqueous solution from the cathode compartment of the electrolytic cell employed in the first reaction zone further contains sodium hypochlorite.

4. The process of claim 2 wherein the first reaction zone is operated at a temperature from about 50° to about 20° F.

5. The process of claim 4 wherein the tertiary alkyl hypochlorite is produced by employing a mole ratio of chlorine to sodium hydroxide from about 0.5:1 to about 1.05:1 and a mole ratio of tertiary alkanol to sodium hydroxide from about 0.75:1 to about 1.1:1.

6. The process of claim 5 wherein the second reaction zone is operated at a temperature from about 32° to about 160° F.

7. The process of claim 6 wherein an effluent containing tertiary alkanol, water, chlorohydrin and organic by-products is withdrawn from the second reaction zone; said effluent being subjected to distillation to recover a water chlorohydrin mixture which is introduced into the third reaction zone, a water-tertiary alkanol mixture which is recycled to the first reaction zone, water which is recycled to the second reaction zone and organic by-products.

8. The process of claim 7 wherein the effluent recovered from the second reaction zone is mixed with cell liquor from the cathode compartment of said electrolytic cell to neutralize hydrogen chloride, and at least a portion of the water recovered from the distillation prior to recycle to the second reaction zone is subjected to evaporation to evaporate water and recover an aqueous brine solution, the evaporated water being recycled to the second reaction zone and the aqueous brine solution being introduced as electrolyte into the electrolytic cell.

9. The process of claim 8 wherein the organic by-products include chlorinated derivatives, and further comprising burning the chlorinated derivatives with molecular oxygen to produce a combustion effluent containing hydrogen chloride;

contacting the combustion effluent with water to absorb the hydrogen chloride and produce a hydrochloric acid solution; and mixing the hydrochloric acid solution with the aqueous brine solution from the first reaction zone prior to introduction into the electrolytic cell.

10. The process of claim 6 wherein the third reaction zone is operated as a stripping zone with epoxy compound being recovered as overhead and aqueous brine as bottoms.

11. The process of claim 6 wherein the olefinically unsaturated compound is propylene.

12. The process of claim 11 wherein the tertiary alkanol is tertiary butyl alcohol.

13. The process of claim 1 wherein the olefinically unsaturated compound has the following structural formula:

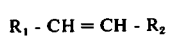

$$R_1 - CH = CH - R_2$$

wherein $R_1$ and $R_2$ are each separately selected from the group consisting of alkyl and phenyl, naphthyl and halo substituted alkyl; phenyl and halo- and alkyl substituted phenyl; naphthyl and halo and alkyl substituted naphthyl; alkenyl and halo substituted alkenyl and wherein $R_1$ and $R_2$ are linked together to form a cycloalkene of from 5 to 10 carbon atoms.

14. The process of claim 1 wherein the olefinically unsaturated compound is styrene.

15. The process of claim 1 wherein the olefinically unsaturated compound is allyl chloride.

16. The process of claim 1 wherein the olefinically unsaturated compound is butadiene.

17. The process of claim 1 wherein the olefinically unsaturated compound is stilbene.

18. The process of claim 1 wherein the olefinically unsaturated compound is an alkene having from 2 to 4 carbon atoms.

* * * * *

UNITED STATES PATENT OFFICE
CERTIFICATE OF CORRECTION

Patent No. 4,008,133            Dated February 15, 1977

Inventor(s) Abraham P. Gelbein et al

It is certified that error appears in the above-identified patent and that said Letters Patent are hereby corrected as shown below:

Column 5, line 10, "fractonal" should be --fractional--;

Column 12, line 27, "as" should be --are--;

Column 13, line 19, "20°F." should be --2 20°F.-- (Claim 4); and

Column 14, line 15, after "stripping" insert --reaction--. (Claim 10).

Signed and Sealed this

Twenty-eighth Day of June 1977

[SEAL]

Attest:

RUTH C. MASON
*Attesting Officer*

C. MARSHALL DANN
*Commissioner of Patents and Trademarks*